United States Patent [19]

DiMenna et al.

[11] 4,454,147
[45] Jun. 12, 1984

[54] NEMATICIDAL 2-CHLORO-5-ARYL-1,3,4-THIADIAZOLES

[75] Inventors: William S. DiMenna, East Amherst; Carmine P. DiSanzo, Medina, both of N.Y.

[73] Assignee: FMC Corporation, Philadelphia, Pa.

[21] Appl. No.: 382,537

[22] Filed: May 27, 1982

[51] Int. Cl.³ .............................................. A01N 43/78
[52] U.S. Cl. .................................................... 424/270
[58] Field of Search ......................................... 424/270

[56] References Cited

U.S. PATENT DOCUMENTS

| | | | |
|---|---|---|---|
| 3,690,858 | 9/1972 | Dahle | 71/67 |
| 3,705,171 | 12/1972 | Papaioannou | 260/306.8 D |
| 3,951,301 | 4/1976 | Meginnis | 220/328 |
| 3,959,301 | 5/1976 | Dahle | 260/302 D |
| 4,061,645 | 12/1977 | Nusslein et al. | 260/302 SD |
| 4,097,669 | 6/1978 | Reisdorff et al. | 542/413 |
| 4,279,907 | 7/1981 | Nusslein et al. | 424/270 |

FOREIGN PATENT DOCUMENTS 2132019  1/1973  Fed. Rep. of Germany ...... 548/136

OTHER PUBLICATIONS

Caveness et al., *Proc. Helm. Soc., Washington*, 22, 87–89 (1955).
*Chem. Abstr.*, 60, 9844c (1964).
*Chem. Abstr.*, 87, 147051x.

Primary Examiner—Allen J. Robinson
Attorney, Agent, or Firm—R. L. Hansen; H. R. Ertelt

[57] ABSTRACT

2-Chloro-5-aryl-1,3,4-thiadiazoles of the formula

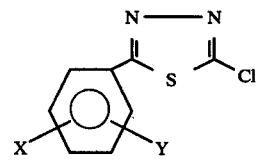

wherein X and Y are independently hydrogen, lower alkyl, lower alkoxy, aryl, substituted aryl, halogen, isothiocyano, trifluoromethylthio, or nitro exhibit nematicidal activity when applied to or incorporated into nematode-infested soil.

14 Claims, No Drawings

NEMATICIDAL 2-CHLORO-5-ARYL-1,3,4-THIADIAZOLES

This invention relates to chemical compositions as well as a method of using the compositions to control nematodes, especially on agricultural crops. More specifically, the nematicidal compositions contain 2-chloro-5-aryl-1,3,4-thiadiazole compounds as the active nematicidal agent.

1,3,4-Thiadiazole is a heterocyclic aromatic organic compound of the following structural formula:

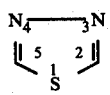

For purposes herein the atoms in the ring are numbered as indicated. 1,3,4-Thiadiazoles have been disclosed in the prior art and are known to be useful in agriculture.

The herbicidal and algicidal utility of certain 2-chloro-5-aryl-1,3,4-thiadiazoles is disclosed in U.S. Pat. No. 3,690,858 and U.S. Pat. No. 3,959,301. The nematicidal use of some 2,5-disubstituted-1,3,4-thiadiazoles has also been described. For example, U.S. Pat. No. 4,279,907 discloses nematicidal activity in certain 5-(thio, sulfinyl or sulfonyl)-2-carboxylic acid derivatives, and U.S. Pat. No. 4,061,645 discloses that certain 2-haloalkyl analogs are nematicides, while U.S. Pat. No. 4,097,669 adds 2-trifluoromethyl analogs. A number of 2-thienyl-5-aryl-1,3,4-thiadiazoles displaying nematicidal activity are disclosed in Chem. Abstr., 60, 9844c (1964).

It has now been found that 2-chloro-5-aryl-1,3,4-thiadiazoles are effective nematicidal agents. These agents are characterized by nematicidal activity at lower application rates, up to 80 times lower than 1,3,4-thiadiazoles disclosed in the prior art. Furthermore, a number of the compounds exhibit good residual activity for at least four weeks following application.

According to the present invention, 2-chloro-5-aryl-1,3,4-thiadiazoles of the following structural formula control nematodes when applied to soil or other locus per se or as suitably formulated nematicidal compositions:

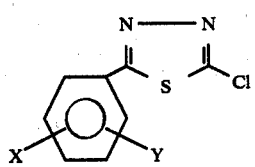

With reference to the aforesaid structural formula, the compounds useful as nematicides include those wherein X and Y are substituents independently selected from hydrogen, lower alkyl, lower alkoxy, aryl, substituted aryl, halogen, isothiocyano, trifluoromethylthio, and nitro, with the proviso that X is not 2-bromo or 3-nitro when Y is hydrogen. For purposes herein, "lower" as used in "lower alkyl" and "lower alkoxy" means a straight or branched chain of 1-7, preferably 1-4, carbon atoms, and "halo" or "halogen" means fluorine, chlorine, and bromine. "Aryl" includes phenyl, diphenyl, naphthyl, and the like, and the substituents in "substituted aryl" include those listed above for X and Y, e.g., lower alkyl, lower alkoxy, halogen, and nitro.

Within the aforesaid description, it is preferred that lower alkyl and lower alkoxy be methyl and methoxy, respectively. Preferred compounds include those wherein Y is H and X is selected from H; —CH₃, especially 4-CH₃; —OCH₃, especially 4—OCH₃; phenyl; and halogen, especially 3-F, 4-F, 4-Cl, and 4-Br; as well as those wherein Y is halogen and X is lower alkyl. Attractive compounds include 2-chloro-5-(4-bromophenyl)-1,3,4-thiadiazole, 2-chloro-5-(4-methylphenyl)-1,3,4-thiadiazole, 2-chloro-5-(4-chlorophenyl)-1,3,4-thiadiazole, and 2-chloro-5-(3-fluoro-4-methylphenyl)-1,3,4-thiadiazole. The last two named compounds are especially useful at very low rates of application.

The nematicidal 2-chloro-5-aryl-1,3,4-thiadiazoles are prepared by the following general method:

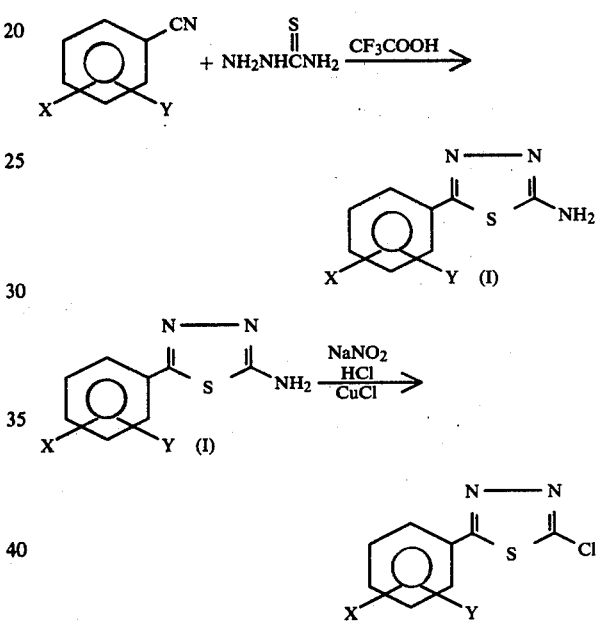

This general procedure was used to prepare the nematicidal 2-chloro-5-aryl-1,3,4-thiadiazoles of Examples 1–18 which follow.

EXAMPLE 1

2-Chloro-5-(4-chlorophenyl)-1,3,4-thiadiazole

To 125 ml of stirred trifluoroacetic acid at room temperature was added 4-chlorobenzonitrile (50.0 g, 0.365 mole), followed by the slow addition of thiosemicarbazide (35.0 g, 0.386 mole). Upon complete addition, the reaction mixture was heated under reflux for 60 hours. The cooled reaction mixture was poured into a mixture of 150 ml of ice and 150 ml of water, then made basic by addition of 150 ml of concentrated ammonium hydroxide. After standing for 16 hours, a crystalline solid was isolated from the mixture by filtration. The solid was recrystallized from 900 ml of ethanol to give 2-amino-5-(4-chlorophenyl)-1,3,4-thiadiazole (27.5 g, mp 227°–229° C.).

Stirred 37% hydrochloric acid, 225 ml, was cooled in a salt-ice bath, and 2-amino-5-(4-chlorophenyl)-1,3,4-thiadiazole (18.3 g, 0.087 mole) was added. The mixture was cooled to −5° C., and a solution of sodium nitrite (25.0 g, 0.338 mole) in 100 ml of water was added dropwise during a one hour period. Upon complete addition, the reaction mixture was allowed to warm to room temperature, where it was stirred for 16 hours. The reaction mixture was heated for one hour on a steam bath, cooled, then filtered to isolate the precipitated solid. The solid was recrystallized from ethanol to give 2-chloro-5-(4-chlorophenyl)-1,3,4-thiadiazole (6.0 g, mp 125°–127° C.).

Analysis—Calc'd for $C_8H_4Cl_2N_2S$: C 41.57; H 1.74; N 12.15. Found: C 41.55; H 1.96; N 12.31.

Similarly, the following compounds were prepared:

| Example | Name | mp (° C.) | Elemental Analysis C | H | N |
|---|---|---|---|---|---|
| 2 | 2-Chloro-5-phenyl-1,3,4-thiadiazole | | | | |
| 3 | 2-Chloro-5-(2-chlorophenyl)-1,3,4-thiadiazole | 94–5 | 41.65 | 1.70 | 12.04 |
| 4 | 2-Chloro-5-(4-bormophenyl)-1,3,4-thiadiazole | 127–8 | 35.07 | 1.66 | 9.92 |
| 5 | 2-Chloro-5-(2-fluorophenyl)-1,3,4-thiadiazole | 79–80.5 | 44.77 | 1.84 | 13.20 |
| 6 | 2-Chloro-5-(3-fluorophenyl-1,3,4-thiadiazole | 79–83 | 43.02 | 2.15 | 12.56 |
| 7 | 2-Chloro-5-(4-fluorophenyl)-1,3,4-thiadiazole | 88–91 | 44.36 | 2.07 | 12.74 |
| 8 | 2-Chloro-5-(4-methylphenyl)-1,3,4-thiadiazole | 70 | | | |
| 9 | 2-chloro-5-(4-methoxyphenyl)-1,3,4-thiadiazole | 92–4 | | | |
| 10 | 2-Chloro-5-(4-nitrophenyl)-1,3,4-thiadiazole | 212–14 | 39.81 | 1.78 | 17.42 |
| 11 | 2-Chloro-5-(3-isothiocyanophenyl)-1,3,4-thiadiazole | 105–107 | 42.50 | 2.20 | 17.28 |
| 12 | 2-Chloro-5-(3-chloro-4-methylphenyl)-1,3,4-thiadiazole | 93–98 | 44.68 | 2.75 | 11.90 |
| 13 | 2-Chloro-5-(3-methyl-4-chlorophenyl)-1,3,4-thiadiazole | 127–128 | 43.73 | 2.42 | 11.49 |
| 14 | 2-Chloro-5-(3-chlorophenyl)-1,3,4-thiadiazole | 95–97 | 41.33 | 1.74 | 11.97 |
| 15 | 2-Chloro-5-(4-[1,1'-biphenyl])-1,3,4-thiadiazole | 139–140 | 61.23 | 3.23 | 10.32 |
| 16 | 2-Chloro-5-(4-trifluoromethylthiophenyl)-1,3,4-thiadiazole | 82–83 | 36.43 | 1.39 | 9.45 |
| 17 | 2-Chloro-5-(3-fluoro-4-methylphenyl)-1,3,4-thiadiazole | 102–104 | 47.04 | 2.66 | 12.24 |
| 18 | 2-Chloro-5-(2-methoxyphenyl)-1,3,4-thiadiazole | 104–105 | 47.79 | 3.24 | 12.49 |

In the normal use of the aforesaid nematicidal 2-chloro-5-aryl-1,3,4-thiadiazoles, the nematicidal compounds usually will not be employed free from admixture or dilution, but ordinarily will be used in a suitable formulated nematicidal composition compatible with the method of application and comprising a nematicidally effective amount of at least one of said nematicidal compounds. Said nematicidal compounds, like most pesticidal agents, may be blended with the agriculturally acceptable surface-active agents and carriers normally employed for facilitating the dispersion of active ingredients, recognizing the accepted fact that the formulation and mode of application of a nematicidal compound may effect the activity of the material. The present nematicidal compounds may be applied, for example, as sprays, dusts, or granules to the area where pest control is desired, the type of application varying of course with the pest and the environment. Thus, the nematicidal compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said nematicidal compounds. The granule particles are relatively large, a diameter of about 400–2500 microns typically. The particles are either inpregnated with the nematicidal compound from solution or coated with the compound, adhesive sometimes being employed. Granules generally contain 0.05–10%, preferably 0.5–5%, active ingredient as the nematicidally effective amount. A typical granular formulation employed for evaluation purposes contains 95% attapulgite clay (24/48 mesh) and 5% 2-chloro-5-(4-chlorophenyl)-1,3,4-thiadiazole.

Dusts are admixtures of said nematicidal compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the nematicide. These finely divided solids have an average particle size of less than about 50 microns. A typical dust formulation useful for controlling nematodes contains by weight 5 parts 2-chloro-5-(4-chlorophenyl)-1,3,4-thiadiazole, 91.2 parts attapulgite clay, 1.9 parts sodium lignosulfonate, and 1.9 parts sodium alkylnaphthalene sulfonate.

The nematicidal compounds of the present invention may be made into liquid concentrates by dissolution or emulsification in suitable liquids and into solid concentrates by admixture with talc, clays, and other known solid carriers used in the pesticide art. The concentrates are compositions containing, as a nematicidally effective amount, about 5–50% the nematicidal compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the nematicidal compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the nematicidal composition.

Other useful formulations include simple solutions of the active ingredient in a solvent in which it is completely soluble at the desired concentration, such as acetone or other organic solvents.

A nematicidally effective amount of said nematicidal compound in a nematicidal composition diluted for application is normally in the range of about 0.001% to about 8% by weight. Many variations of spraying and dusting compositions known in the art may be used by substituting said nematicidal compounds of this invention into compositions known or apparent to the art.

The nematicidal compositions of this invention may be formulated with other active ingredients, including insecticides, other nematicides, acaricides, fungicides, plant growth regulators, fertilizers, etc. In using the compositions to control nematodes, it is only necessary that a nematicidally effective amount of at least one of said nematicidal compounds be applied to the locus where control is desired, generally a soil locus where agricultural crops are grown. When applied to soil, it is advantageous to mix or incorporate the nematicidal compound into the soil. Liquid nematicidal compositions may be injected into the soil is fumigants or sprayed on the surface. Solid compositions may be applied by broadcasting or in bands. For most applications, a nematicidally effective amount will be about 2 to 12 kg per hectare.

The nematicidal compounds were evaluated for nematicidal activity against the root-knot nematode (*Meloidogyne incognita*), the stunt nematode (*Tylenchorhynchus claytoni*), and the lesion nematode (*Pratylenchus penetrans*) using aqueous acetone solutions or 5 weight percent dust formulations made up as follows and ground to fine powders:

| Nematicidal compound (100% active basis) | 5 parts |
|---|---|
| Base | 95 parts |
| 96%-attapulgite clay | |
| 2%-highly pruified sodium lignosulfonate (100%) | |
| 2%-powdered sodium alkylnaphthalenesulfonate (75%) | |

The formulations were tested for activity against root-knot nematode as follows:

Samples of root-knot nematode inoculum were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", *Proc. Helm. Soc., Washington*, 22, 87-89 (1955)] and mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infested was used for soil-incorporated nematicidal studies within 2 days of preparation. The infested soil was treated with formulations to be tested for nematicidal activity by incorporating the formulation in the soil at 25 ppm or less (weight active compound in mg/soil volume in liters). Young tomato plants were planted in this treated, infested soil in three-inch pots. Check plants were planted in the same manner, except untreated, infested soil was used. The formulation base, without active ingredient, was added to infested soil separately and tomato plants grown therein to detect the effects, if any, of chemicals in the formulation base.

At the end of two weeks the roots of all plants were examined and evaluated for galling in comparison to untreated check plants. The results of the tests were expressed in terms of a "Knot Index", a knot index of 4 signifying no control, 3 signifying 25% less swelling on the treated roots than the untreated roots, 2 signifying 50% less swelling, 1 signifying 75% less swelling, and 0 signifying complete control. Between 1 and 0, a knot index of 0.8, 0.5, and 0.4-0.1 signifies 80%, 90%, and 95-99% control, respectively. The results of tests at various rates of application against the root-knot nematode using a number of nematicidal 2-chloro-5-aryl-1,3,4-thiadiazoles appear in Table 1.

Evaluation of compositions of the invention against stunt nematode was carried out by incorporating formulations in soil at various concentrations and then planting a corn seedling therein. Two days thereafter the soil was inoculated with stunt nematode in mixed stages of growth, from larvae to adults. The soil was evaluated for nematode population approximately five weeks after treatment. Untreated check plants showed no nematode control. Results are recorded in Table 2 as "Percent Control" relative to nematode control in the untreated check pot. The results appear in Table 2.

Compositions were also evaluated against lesion nematode, following a procedure similar to that for stunt nematode, but in which pea seedlings were planted instead of corn seedlings, and nematodes were extracted from the root systems, instead of from the soil. Untreated plants showed no nematode control. Results with formulations of the invention are recorded in Table 3.

TABLE 1

| Evaluation Against Root-Knot Nematode | | |
|---|---|---|
| Compound of Ex. | Rate of Application | Knot Index[a] |
| 1 | 10 ppm | 0 |
| | 5 | 0 |
| | 2.5 | 0 |
| 2 | 10 | 0.2 |
| | 5 | 1.3 |
| | 2.5 | 1.2 |
| 3 | 25 | 3.3 |
| | 10 | 4.0 |
| 4 | 25 | 0 |
| | 10 | 0.5 |
| | 5 | 1.0 |
| 5 | 25 | 0.5 |
| | 10 | 1.6 |
| | 5 | 4.0 |
| 6 | 10 | 0.4 |
| | 5 | 2.8 |
| | 2.5 | 4.0 |
| 7 | 10 | 0.3 |
| | 5 | 0.8 |
| | 2.5 | 2.5 |
| 8 | 10 | 0 |

TABLE 1-continued

Evaluation Against Root-Knot Nematode

| Compound of Ex. | Rate of Application | Knot Index[a] |
|---|---|---|
|  | 5 | 0.1 |
|  | 2.5 | 1.0 |
| 9 | 10 | 0.9 |
|  | 5 | 2.4 |
|  | 2.5 | 4.0 |
| 10 | 25 | 3.0 |
|  | 10 | 2.0 |
| 11 | 25 | 1.50 |
|  | 10 | 4.00 |
|  | 5 | 4.00 |
| 12 | 25 | 0.58 |
|  | 10 | 1.75 |
|  | 5 | 3.00 |
| 13 | 25 | 0.90 |
|  | 10 | 3.00 |
|  | 5 | 4.00 |
| 15 | 25 ppm | 0.58 |
|  | 10 | 1.25 |
|  | 5 | 3.00 |
| 16 | 25 | 0 |
|  | 10 | 0.70 |
|  | 5 | 3.50 |
| 17 | 25 | 0 |
|  | 10 | 0 |
|  | 5 | 0 |
| 18 | 25 | 0.50 |
|  | 10 | 2.00 |
|  | 5 | 4.00 |

[a]Average of several experiments in some cases.

TABLE 2

Evaluation Against Stunt Nematode

| Compound Number | Rate of Application | Percent Control[a] |
|---|---|---|
| 1 | 15 ppm | 99.4 |
| 2 | 15 | 100 |
|  | 10 | 97.7 |
| 4 | 15 | 89.5 |
| 6 | 15 | 62.0 |
| 7 | 15 | 76.8 |
| 8 | 15 | 97.3 |
| 9 | 15 | 93.6 |

[a]Percent Control =
$$\left[\frac{\text{Average Population Count in the Check} - \text{Average Population Count in the Treatment}}{\text{Average Population Count in the Check}}\right] \times 100$$

TABLE 3

Evaluation Against Lesion Nematode

| Compound Number | Rate of Application | Percent Control[a] |
|---|---|---|
| 1 | 15 ppm | 85.9 |
| 2 | 15 | 97.2 |
|  | 10 | 79.4 |
| 4 | 15 | 73.4 |
| 8 | 15 | 45.9 |
| 9 | 15 | 56.2 |

[a]Percent Control =
$$\left[\frac{\dfrac{\text{Population count in check*}}{\text{Weight of roots in check plant}} - \dfrac{\text{Population count in treatment*}}{\text{Weight of roots in treated plants}}}{\dfrac{\text{Population Count in check}}{\text{Weight of Roots in Check Plant}}}\right] \times 100$$

*Average of 3–4 Replicates

What is claimed is:

1. A nematicidal composition comprising in admixture with an agriculturally acceptable carrier a nematicidally effective amount of at least one nematicidal compound of the formula

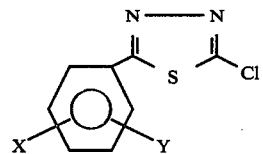

wherein X and Y are substituents independently selected from the group consisting of lower alkoxy, phenyl, isothiocyano, trifluoromethylthio, and nitro; or Y is hydrogen and X is selected from the group consisting of lower alkoxy, phenyl, isothiocyano, trifluoromethylthio, 2-nitro, and 4-nitro.

2. A nematicidal composition of claim 1 wherein Y is hydrogen and X is selected from the group consisting of methoxy and phenyl.

3. A nematicidal composition of claim 1 wherein Y is H and X is 4-OCH$_3$.

4. A nematicidal composition of claim 1 wherein Y is H and X is phenyl.

5. A method of controlling nematodes which comprises applying to or incorporating into nematode-infested soil a nematicidally effective amount of at least one nematicidal compound of the formula

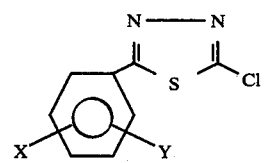

wherein X and Y are substituents independently selected from the group consisting of hydrogen, lower alkyl, lower alkoxy, phenyl, halogen, isothiocyano, trifluoromethylthio, and nitro, with the proviso that X is not 2-Br or 3-NO$_2$ when Y is hydrogen.

6. A method according to claim 5 wherein either Y is hydrogen and X is selected from the group consisting of hydrogen, methyl, methoxy, phenyl, and halogen, or Y is halogen and X is lower alkyl.

7. The method of claim 5 wherein Y is H and X is 4-CH$_3$.

8. The method of claim 5 wherein Y is H and X is 4-OCH$_3$.

9. The method of claim 5 wherein Y is H and X is 3-F.

10. The method of claim 5 wherein Y is H and X is 4-F.

11. The method of claim 5 wherein Y is H and X is 4-Cl.

12. The method of claim 5 wherein Y is H and X is 4-Br.

13. The method of claim 5 wherein Y is H and X is phenyl.

14. The method of claim 5 wherein Y is 3-F and X is 4-CH$_3$.

* * * * *